(12) United States Patent
Le et al.

(10) Patent No.: US 7,749,711 B2
(45) Date of Patent: Jul. 6, 2010

(54) METHODS OF ASSESSING ENDOTHELIAL DYSFUNCTION USING ACUTE TRANSIENT RESPONSES FOLLOWING FAT ADMINISTRATION

(76) Inventors: Ngoc Anh Le, 1779 Lavista Oaks Dr., Decatur, GA (US) 30033; W. Virgil Brown, 3208 Habersham Rd., Atlanta, GA (US) 30305

( * ) Notice: Subject to any disclaimer, the term of this patent is extended or adjusted under 35 U.S.C. 154(b) by 870 days.

(21) Appl. No.: 10/527,510

(22) PCT Filed: Sep. 11, 2003

(86) PCT No.: PCT/US03/28525

§ 371 (c)(1),
(2), (4) Date: Mar. 31, 2006

(87) PCT Pub. No.: WO2004/025255

PCT Pub. Date: Mar. 25, 2004

(65) Prior Publication Data

US 2006/0205009 A1    Sep. 14, 2006

(51) Int. Cl.
G01N 33/53    (2006.01)
(52) U.S. Cl. .................. 435/7.1; 435/7.2; 435/7.91; 435/7.92
(58) Field of Classification Search .................. None
See application file for complete search history.

(56) References Cited

OTHER PUBLICATIONS

Takanair et al. Clinica Chimica Acta 2007 vol. 381, p. 179-181.*
Ryan et al. Q J Med 1998. vol. 91, p. 411-415.*
Billman et al. (Circulation 1999 vol. 99, p. 2452-2457).*
Avogaro P, Bittolo B, Cazzolato G. Presence of a modified LDL in humans. Arteriosclerosis. 1988; 8:79-87.
Esterbauer H, gebicki J, Puhl H, and Jurgens G. The role of lipid peroxidation and antioxidants in oxidative modification of LDL. Free Radical Biol Med. 1992; 13:341-390.
Gradek, W. et al. Polyunsaturated fatty acids acutely suppress antibodies to malondialdehyde-modified lipoproteins in patients with vanscular disease. The American Journal of Cardiology vol. 93. 2004; pp. 881-885.
Holvoet P, Perez G, Zhao Z, et al. Malondialdehyde-modified LDL in patients with atherosclerotic disease. J Clin Invest. 1995; 95:261 1-2619.
Le Na, Li X, Kyung S, Brown WV. Evidence for the vivo generation of oxidatively modified epitopes in patients with atherosclerotic endothelium. Metabolism: Clinical & Experimental. 200; 49(10):1271-7.
Ludmer PL, Selwyn AP, Shook TL, Wayne RR, Medge GH, Alexander RW, Ganz P. Paradoxical vasoconstriction induced by acetylcholine in atherosclerotic coronary articles. NEJM. 1986; 315:1046-105.
Nable EG, Selwyn AP, Ganz P. Large coronary arteries in humans are responsive to changing blood flow: and endothelium-dependent mechanism that fails in patients with atherosclersis. J AM Call Cardiol. 1994; 16:349-356.
Pentilainen MO, R Oksjoki, K Oorni and PT Kovanen (2002) Lipoprptein lipase in the arterial wall: Linking LDL to the arterial extracellular matrix and much more. ATVB 22:211-217.
Ross R (1999) Mechanisms of Disease: Atherosclerosis-an inflammatory disease. NEJM 340: 115-149.
Treasure CB, Klein JL, Weintraub WS, Talley JD, Stillabower ME, Kosinski AS, Zhang J, Boccuzzi SJ, Cedarholm JC, Alexander RW. Beneficial effects of cholesterol-lowering therapy on the coronary endothelium in patients woth coronary artery disease. NEJM. 1995; 332(8):481-7.
Vogel RA (1997) Coronary risk factors, endothelial function and atherosclerosis: a review. Clin Cardiol 20: 426-432.
Wilkinson I, Qasem A, McEniery C, Webb D, Avolio A, Cockcroft J. Nitric Oxide Regulates Local Arterial Distensibility in Vivo. Circulation 2002; 105:213-217.
Wilson, Peter WF, D'Agostino, R, Levy, D, Belanger, A., Silbershatz, H, Kannel, W. Prediction of Coronary Heart Disease Using Risk Factor Categories. Circulation 1998; 97 918):1837-1847.
Yla-Herttuala S, Palinski W, Butler S, et al. Rabbit and human atherosclerotic lesions contain lgG that recognizes epitopes of oxidized LDL. Arthioscler Thromb. 1994; 14:32-40.
Yla-Herttuala S, Palinski W, Rosenfeld M, et al. Evidence for the presence of oxidatively modified LDL in atherosclerotic lesions of rabbit and man. J Clin Invest. 1989; 84:1086-1095.
Zilversmit DB (1973) A proposal linking atherogenesis to the interaction of endothelial lipase with TG-rich lipoproteins. Circ res 33: 633-638.
Zilvermit DB (1979) Atherogenesis: a postprandial phenomenon. Circulation 60: 473-485.

(Continued)

Primary Examiner—Jacob Cheu
(74) Attorney, Agent, or Firm—Ping Wang; Morris, Manning & Martin, LLP

(57) ABSTRACT

The present invention provides methods utilizing the fat-induced antibody response (FIAR) to assess endothelial function. Additional methods are provided that utilize FIAR for diagnosing and monitoring the progression of vascular diseases, the success of treatment for these diseases, and as a measure of the oxidative stress imposed upon vascular endothelium. Still more methods are provided for measuring the oxidation products of lipids in blood following the administration of a polyunsaturated fatty acid (fat-induced acute response) to monitor the treatment success of a vascular disease, for monitoring the degree of endothelial inflammation, and for diagnosing and monitoring the progression of a cardiovascular disease.

10 Claims, 9 Drawing Sheets

OTHER PUBLICATIONS

Tinahones et al. Increase levels of anti-oxidized low-density lipoprotein andtibodies are associated with reduced levels of cholesterol in the general population. Metabolism Apr. 2002, vol. 51, No. 4, pp. 429-431, whole document, especially see Discussion.

Hulthe et al. Relationship between C-reactive protein and intima-media thickness in the carotid and femoral arteries and to antibodies against oxidized low-density lipoprotein in healthy men; the atherosclerosis and insulin resistance study. Clinical Science 200 vol. 100, pp. 371-378, whole document.

Tanaga et al. Increased circulating malondial dehyde-modified LDL levels in patients with coronary artery diseases and their associated with peak sizes of LDL particles. Apr. 2002 vol. 4, pp. 662-666, whole document.

Alberti A., Bolognini L., Macciantelli D., and Caratelli M. The Radical Cation of N, N-Diethyl-Pap-Phenylendiamine: A Possible Indicator of Oxidative Stress in Biological Samples. Res. Chem. Intermed. 200 vol. 26(3):253-267.

Ginsberg HN., N-A Le, and JC Gibson (1985) Regulation of the Production and Catabolism of Plasma LDL in Hypertriglyceridemic Subjects: Effects of Weight Loss. JCI 75:614-622.

Takanari Nakano, et al., "Immunoreactive circulating oxidized HDL concentration do not increase in patients undergoing carotid endarterectomy: A comparitive study for oxidized HDL and oxidized LDL concentrations in plasma", Clinica Chimica Acta, vol. 381, pp. 179-181, 2007.

M. Ryan, et al., "Antibodies to oxidized lipoproteins and their relationship to myocardial infarction", Q J Med, vol. 91, pp. 411-415, 1998.

* cited by examiner

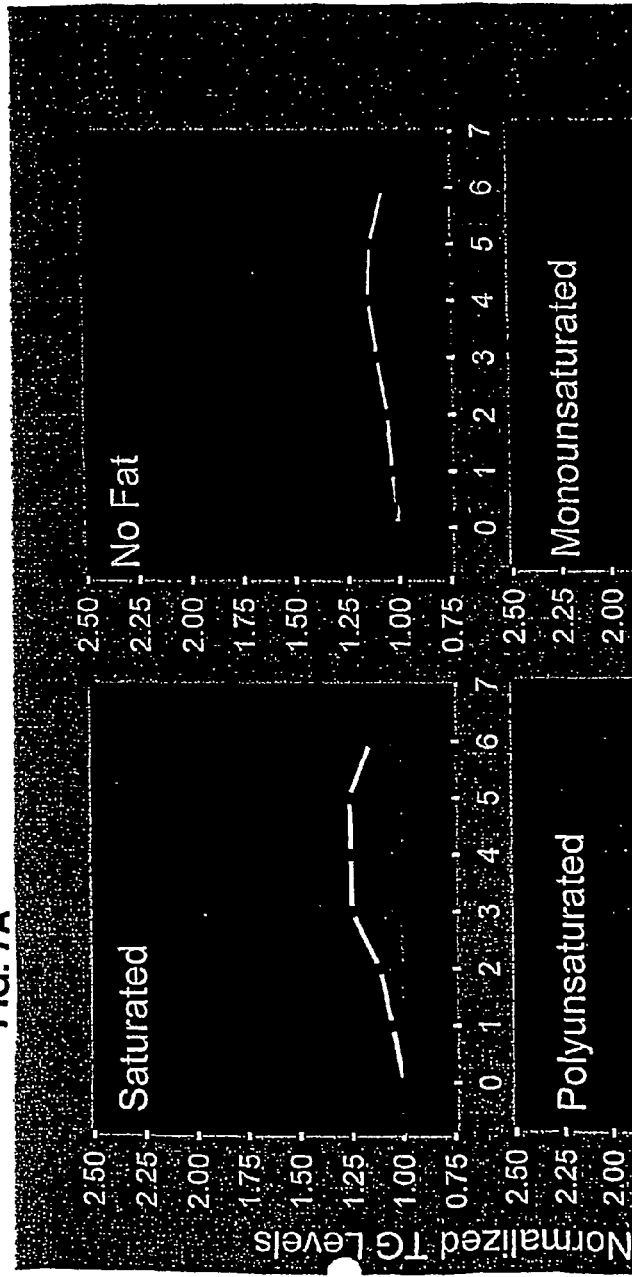

METHODS OF ASSESSING ENDOTHELIAL DYSFUNCTION USING ACUTE TRANSIENT RESPONSES FOLLOWING FAT ADMINISTRATION

This application is being filed on 11 Sep. 2003 as a PCT International Patent application in the name of Emory University, a U.S. national corporation, applicant for the designation of all countries except the US, and Ngoc-anh Le and Virgil W. Brown, both US citizens, applicants for the designation of the US only.

FIELD OF THE INVENTION

This invention relates generally to methods of assessing endothelial function in a living subject.

BACKGROUND OF THE INVENTION

Vascular dysfunction accompanies the active disease process of atherosclerosis and is determined in large part by endothelial cell dysfunction (Ludmer et al., 1986; Nabel et al., 1994; Treasure et al., 1995; and Wilkinson et al., 2002). This impairment is due, in part, to the generation of oxygen radicals, such as superoxide anion ($O_2$), peroxynitrite or hydrogen peroxide ($H_2O_2$), which create a highly oxidative environment. Oxygen radicals are produced by the endothelium and other vascular cells under the influence of cytokines as a major causative component of the atherosclerotic process.

Proteins and lipids in this environment are altered in a variety of ways. One class of biological compounds that are most vulnerable to oxidation is the group of polyunsaturated fatty acids that exist in cell membranes and in circulating lipoproteins. This reaction generates a series of reactive aldehydes that form covalent bonds with other molecules in the immediate environment. One of the most common reactions appears to be that with the epsilon amino group of the lysine side chains, which exist as components of nearby proteins. This generates a new surface epitope on the protein, which is immunogenic. The occurrence of circulating antibodies to malondialdehyde (MDA)-lysine side groups on proteins seems to be ubiquitous among humans and is commonly found in animals as well (Avogaro et al., 1988; Yla-Herttuala et al., 1989; Holvoet et al., 1995; and Yla-Herttuala et al., 1994).

Arteriosclerosis means hardening of the arteries and is a generic term for three patterns of vascular disease that have in common thickening and loss of elasticity of arterial walls. The dominant pattern is atherosclerosis, characterized by the formation of intimal fibrous plaques that often have a central core rich in lipid. The second morphologic form of atherosclerosis is characterized by calcified deposits in medium-sized muscular arteries in persons older than 50 years. These lesions typically do not encroach on the vessel lumen. Arteries affected may also develop atherosclerosis. The third type affects small arteries and arterioles and is termed arteriolosclerosis. This involves thickening of vessel walls with luminal narrowing that may induce downstream ischemic injury. Arteriolosclerosis is most often associated with hypertension and diabetes.

Atherosclerosis is characterized by intimal lesions called atheromas or fibro-fatty plaques that protrude into the lumen, weaken the underlying media, and undergo a series of complications. Atherosclerosis primarily affects elastic arteries (e.g., aorta, carotid and iliac arteries) and large and medium-sized muscular arteries (e.g., coronary and popliteal arteries). The disease often begins in childhood, but symptoms are not usually evident until middle age or later when the arterial lesions precipitate organ injury. Although any organ or tissue in the body may be so involved, symptomatic atherosclerosis disease is most often localized to the arteries supplying the heart, brain, kidneys, lower extremities, and small intestine. Myocardial infarction (heart attack), cerebral infarction (stroke), and aortic aneurysms are the major consequences of this disease.

The key processes in atherosclerosis are intimal thickening and lipid accumulation, producing the characteristic atheromatous plaques. The atheromatous plaque is the basic lesion consisting of a raised focal plaque within the intima, having a core of lipid (mainly cholesterol and cholesterol esters) and a covering fibrous cap. Also called fibrous, fibro-fatty, lipid, or fibrolipid plaques, atheromatous plaques appear white to whitish yellow and impinge on the lumen of the artery. They vary in size from approximately 0.3 to 1.5 cm in diameter but sometimes coalesce to form larger masses. The distribution of atherosclerotic plaques in humans is characteristic. The abdominal aorta is usually much more involved than the thoracic aorta, and aortic lesions tend to be much more prominent around the origins (ostia) of its major branches. Atherosclerotic plaques have three principal components: (1) cells, including smooth muscle cells, macrophages, and other leukocytes; (2) connective tissue extracellular matrix, including collagen, elastic fibers, and proteglycans; and (3) intracellular and extracellular lipid deposits. Fatty streaks are also often observed in the lumen of blood vessels and may be precursors of atheromatous plaques. The streaks begin as multiple yellow, flat spots (fatty dots) less than 1 mm in diameter that coalesce into elongated streaks, 1 cm long or longer. Fatty streaks are composed of lipid-filled foam cells with T lymphocytes and extracellular lipid present in smaller amounts than in plaques. Fatty streaks appear in the aortas of some children younger than 1 year of age and all children older than 10 years, regardless of geography, race, sex, or environment. Coronary fatty streaks are less common than aortic but begin to form in adolescence, and they occur at the same anatomic sites that are later prone to develop plaques. Although fatty streaks may be precursors of plaques, not all fatty streaks are destined to become fibrous plaques or more advanced lesions.

Despite the information known regarding the pathophysiology of atherosclerosis, in clinical trials of efficacious treatments, there is little available to the clinician to determine early in the course of treatment which patients have altered endothelial pathophysiology. No test or assay is currently available that can be used for adjusting treatments to achieve a "normal result" that predicts the expected improvement in long-term outcome.

Therefore, a heretofore-unaddressed need exists in the art to address the aforementioned deficiencies and inadequacies.

SUMMARY OF THE INVENTION

Embodiments of the present invention provide methods of assessing endothelial function and for diagnosing and monitoring the progression of vascular diseases and their treatments thereof following an acute response to a fat challenge.

In one aspect, the invention is related to a method of diagnosing and monitoring the progression of a vascular disease in a living subject. The method includes the following steps: (a) measuring the amount of endogenous circulating antibodies directed against an oxidatively damaged lipoprotein in a sample of blood taken from a living subject; (b) administering a polyunsaturated fatty acid either orally or intravenously (as a triglyceride or phospholipid emulsion); (c) measuring the amount of the endogenous circulating antibodies in a second sample of blood taken from a living subject; and (d) correlating the change in the amount of the endogenous circulating antibodies with the severity of the vascular disease.

In various aspects of the methods of the present invention, the endogenous antibody is directed against at least one type of lipoprotein including low-density lipoprotein, high-density lipoprotein, intermediate density lipoprotein, and very low-density lipoprotein. In a preferred embodiment, the antibody is directed against a low-density lipoprotein. In a more preferred embodiment, the antibody is directed against oxidatively damaged malondialdehyde-modified low-density lipoprotein. In still other aspects of the present invention, the antibody measured is an IgG-low-density lipoprotein complex.

The present invention also provides a method of monitoring the progression of vascular disease treatment in a living subject that includes the steps of (a) administering a polyunsaturated fatty acid; (b) measuring the amount of lipid oxidation products in a blood sample taken from the subject; and (c) correlating the amount of lipid oxidation products in the blood sample with the success or failure of the vascular disease treatment.

In various aspects of the present invention, the lipid oxidation product measured is at least one of malondialdehyde-modified low-density lipoprotein, oxidized low-density lipoprotein, 4-hydroxynonenal-low-density lipoprotein, acetyl-low-density lipoprotein, acrolein-low-density lipoprotein, oxidized arachidonic acid-modified low-density lipoprotein, oxidized linoleic acid modified low-density lipoprotein, lipoperoxide, cardiolipin, oxidized cholesterol, oxidized choleosteryl lineolate, and oxidized triglyceride.

Other aspects of the present invention provide a method of monitoring the degree of oxidative stress in a living subject by the steps of (a) administering a polyunsaturated fatty acid; (b) measuring the amount of lipid oxidation products in a blood sample; and (c) correlating the amount of lipid oxidation products in the blood sample with the degree of oxidative stress.

Yet another aspect of the present invention provides for a method of monitoring the progression of a vascular disease as an indicator of the success or failure of a medical treatment in a living subject by the steps of: (a) administering a polyunsaturated fatty acid; (b) measuring the amount of lipid oxidation products in a blood sample; and (c) correlating the amount of lipid oxidation products in the blood sample with the success or failure of the medical treatment. In various aspects, the medical treatment that can be monitored is for the treatment or alleviation of at least one of the following: treatment or alleviation of hypercholesterolemia, hypertension, cigarette smoking, diabetes, angina, menopause, hormonally based birth control, cancer, stroke, homocystinuria, thrombosis, vasculitis, cardiomyopathy, endocarditis, an autoimmune disease and a neurological disorder.

The present invention also provides a method of monitoring the degree of endothelial inflammation in a living subject by the steps of (a) administering a polyunsaturated fatty acid; (b) measuring the amount of lipid oxidation products is a blood sample; and (c) correlating the amount of lipid oxidation products in the blood sample with the degree of endothelial inflammation.

Also provided by the present invention are methods of diagnosing and monitoring the progression of a cardiovascular disease in a living subject by the steps of (a) measuring the amount of endogenous circulating antibodies directed against an oxidatively damaged lipoprotein in a sample of blood; (b) administering a polyunsaturated fatty acid; (c) measuring the amount of said endogenous circulating antibodies in a second sample of blood; and (d) correlating the change in the amount of said endogenous circulating antibodies with the severity of the cardiovascular disease.

In further aspects, the present invention provides for a method of diagnosing and monitoring the progression of a cardiovascular disease in an a living subject includes the steps of (a) administering a polyunsaturated fatty acid; (b) measuring the amount of lipid oxidation products is a blood sample; and (c) correlating the amount of lipid oxidation products in the blood sample with the severity of a cardiovascular disease.

In practicing the present invention, a living subject can be an animal or human being.

BRIEF DESCRIPTION OF THE DRAWINGS

FIGS. 7A-D show normalized auto-antibody (AAb) levels following a saturated fat (A), carbohydrate only (no fat; B), polyunsaturated fat (C) and monounsaturated fat (D) meal.

DETAILED DESCRIPTION OF THE PREFERRED EMBODIMENTS

Various embodiments of the invention are now described in detail. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

DEFINITIONS

"Auto-antibody" or "AAb" or "endogenous circulating antibody" refers to any antibody generated against oxidated epitopes or portions of any lipoprotein following their interaction with diseased or dysfunctional vascular epithelium. One non-limiting example includes antibodies directed against malondialdehyde (MDA) modified low-density lipoproteins;

"Polyunsaturated fatty acid" or "PUFA" refers to any unsaturated fatty acid containing more than one double bond per molecule. Non-limiting examples of polyunsaturated fatty acids include oleic acid, linoleic acid and linolenic acid.

"A living subject" or "a subject" refers to any animal or a human.

Figure 2:
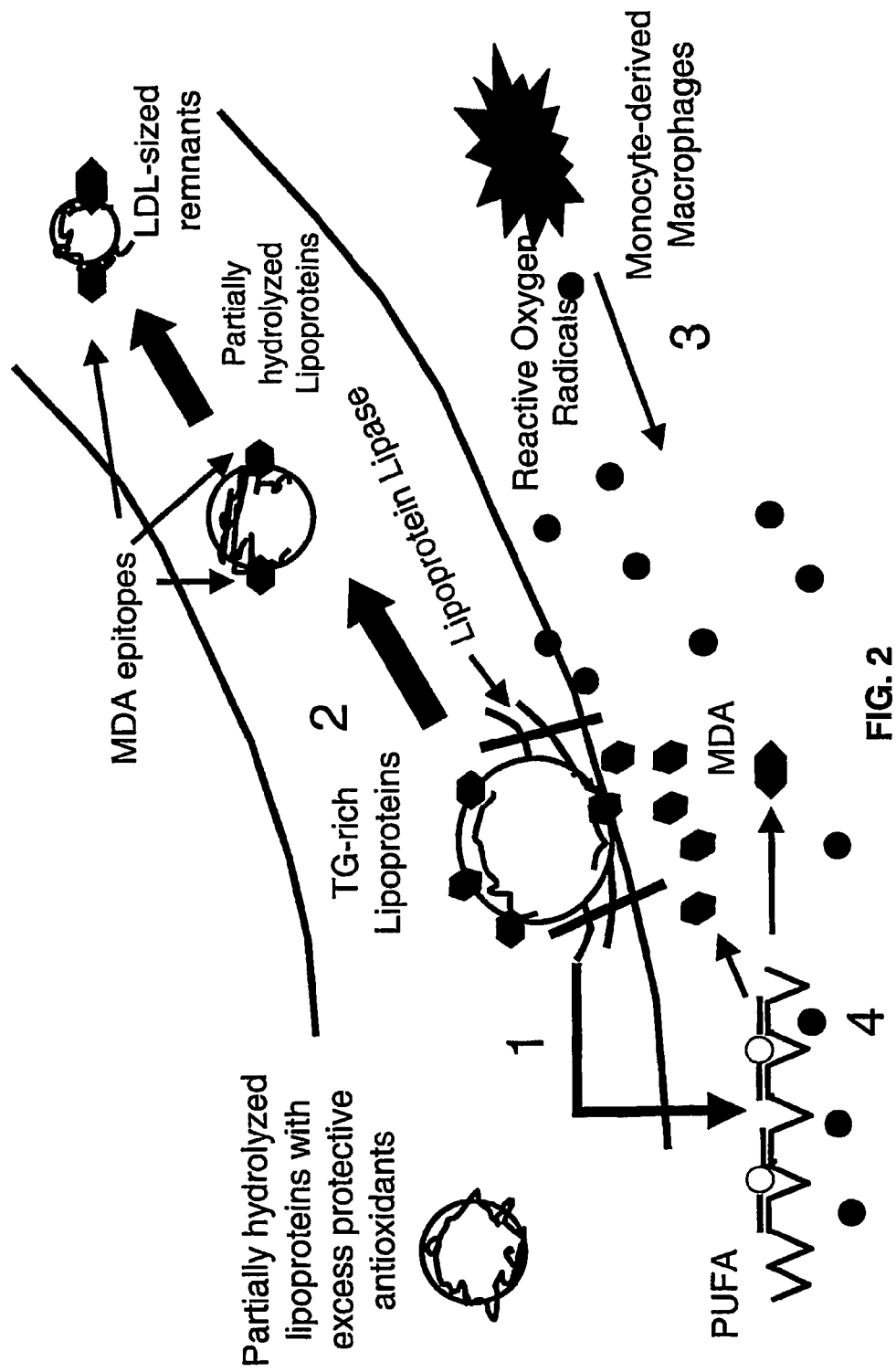
FIG. 2 depicts one possible hypothesis for the oxidative processes that are thought to affect to circulating LDL.

Vascular dysfunction accompanies the active disease process of atherosclerosis and is determined in large part by endothelial cell dysfunction. This dysfunction may result from the induction of a highly oxidative state within the endothelial cells overlying active atherosclerotic lesions. The generation of reactive oxygen species (ROS) such as superoxide anion ($O_{2-}$ and hydrogen peroxide ($H_2O_2$) changes intracellular metabolism and generates a reactive oxidative state on the cell surface. Polyunsaturated fatty acids that exist in cell membranes and in circulating lipoproteins are particularly vulnerable to oxidation. This is depicted schematically in FIG. 2. In this schema, as triglyceride-rich lipoproteins interact with lipoprotein lipase anchored to the walls of blood vessels, they form tight junctions with the endothelium. In patients with developing atherosclerosis, the subendothelial space has been invaded by proliferating monocyte-derived macrophages (Ross, 1999; Vogel, 1997) that are secreting cytolines and reactive oxygen species, ROS. An impaired reactive response of the diseased artery has been linked to excess generation of ROS and impaired function of the nitric oxide system. Retention of triglyceride-rich lipoproteins to the endothelium by proteoglycans (Pentikainen et al., 2002) is likely to promote the transfer of ROS to plasma lipoproteins. With the removal of triglyceride, the triglyceride-rich lipoproteins become smaller and more dense. If there is adequate antioxidant protection on the particle, the newly acquired ROS would be quenched resulting in the formation of a normal particle as shown in Pathway 1 in FIG. 2. If, however, inadequate antioxidant reserve is available, propagation of the oxidative modification may proceed resulting in the formation of oxidized LDL if the triglyceride-rich lipoprotein is VLDL (Pathway 2, FIG. 2). The average conversion time for VLDL to LDL is 3-5 hours, and would be adequate to complete the oxidation of protein as suggested by in vitro data (Ginsberg et al., 1985). In the case of the healthy endothelium, there is no excess generation of ROS and the triglyceride-rich lipoproteins would not pick up any oxidatively-modified epitopes. This would be consistent with a role of postprandial lipoproteins in atherosclerosis (Zilversmit, 1973; Zilversmit, 1979).

Antibodies to oxidized lipoproteins, specifically malondialdehyde (MDA) modified low-density lipoproteins have been found to be nearly ubiquitous among humans and have been shown by the inventors to be transiently reduced in the blood of patients with atherosclerosis following the ingestion of a fat-laden meal (Le et al., 2000). This phenomenon has been termed the fat-induced antibody response (FIAR). The present invention provides methods utilizing the FIAR that assess endothelial function. Additional methods are provided that utilize FIAR for diagnosing and monitoring the progression of vascular diseases, the success of treatment for these diseases, and as a measure of the oxidative stress imposed upon the endothelium.

Additionally, the inventors have discovered that the acute reduction in auto-antibodies after the fat ingestion is a reflection of an imbalance between the auto-antibodies and the newly-generated oxidative epitopes, which in turn, is a reflection of inflammation of the endothelium, resulting in the excess formation of reactive oxygen species and lipid oxidation products. This alteration in the levels of lipid oxidation products in particular, following an ingestion of polyunsaturated fat, has been termed the fat-induced acute response. Thus, still more methods are provided for measuring the oxidation products of lipids in blood following the administration of a polyunsaturated fatty acid to monitor the treatment success of a vascular disease, for monitoring the degree of endothelial inflammation, and for diagnosing and monitoring the progression of a cardiovascular disease.

Endothelial Function

The methods of the present invention relate generally to methods of assessing endothelial function. More specifically, the present invention provides a method of diagnosing and monitoring the progression of a vascular disease. In another embodiment, a method is provided for monitoring the progression of vascular disease treatment. Still another embodiment provides a method of monitoring the degree of oxidative stress in an animal. Yet another method is provided for monitoring the progression of a vascular disease as an indicator of the success or failure of a medical treatment in a living subject. Another embodiment provides for a method of monitoring the degree of endothelial inflammation. Still other embodiments provide for a method of diagnosing and monitoring the progression of a cardiovascular disease.

Endothelial dysfunction and the excess generation of oxidated lipoproteins are thought to contribute to a variety of diseases including, but not limited to, atherosclerosis, angina, stroke, cardiomyopathy, endocarditis, and coronary heart disease and neurological disorders such as Parkinson's disease or Alzheimer's. Furthermore, a variety of diseases or pathological states may themselves contribute to endothelial dysfunction. These include, but are not limited to, the state of endothelial stress, hypertension, diabetes, cigarette smoking, hypercholesterolemia, menopause, hormonally based birth control, cancer, homocystinuria, thrombosis, vasculitis, and autoimmune diseases or states. By treating or alleviating one of these contributing factors, it is possible to prevent or halt subsequent endothelial damage or injury. Monitoring the treatment or alleviation of one of these contributing factors, thus may provide insight as to the state of the endothelial damage.

Figure 1:
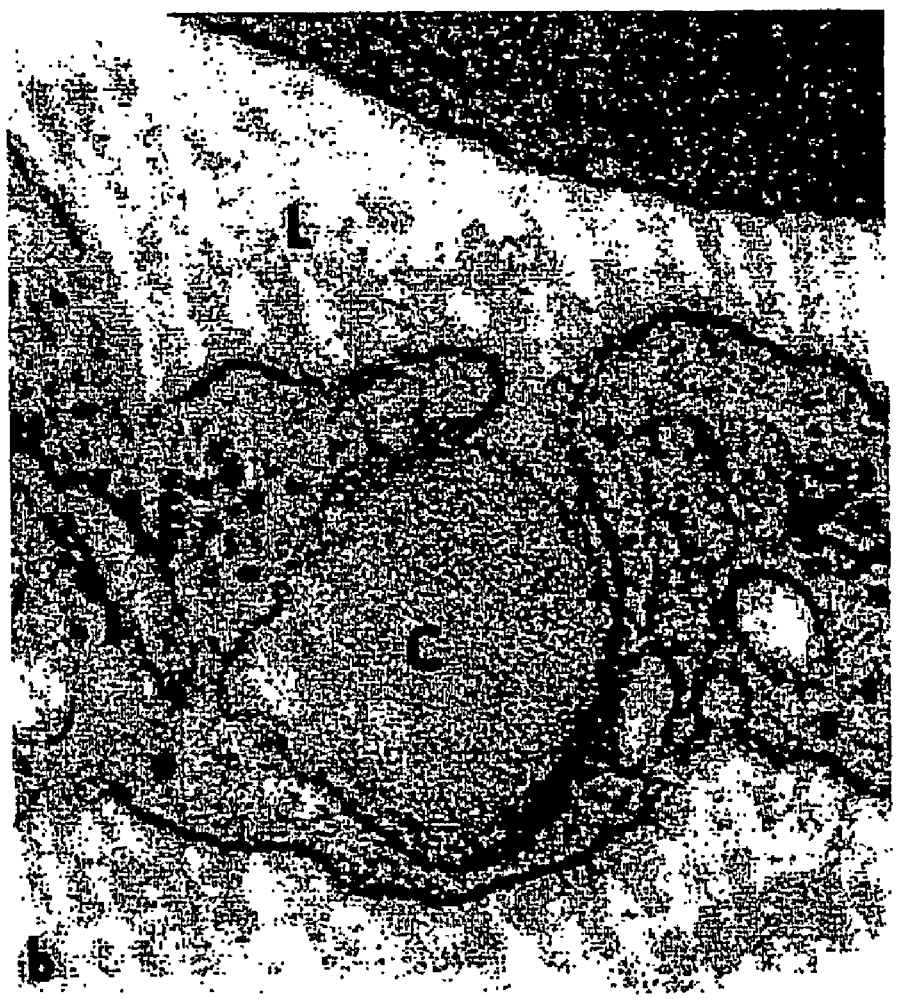
FIG. 1 is an electron photomicrograph that illustrates the close contact between the chylomicron particle (C) carrying newly absorbed dietary fats and the endothelium (E).

Current views of atherosclerosis consider this disease to be a result of a response to injury. Thus, atherosclerosis is considered to be a chronic inflammatory response of the arterial wall initiated by some form of injury to the endothelium. Central to this thesis are the following events that may begin with the development of focal regions of chronic endothelial injury, usually subtle, with resultant endothelial dysfunction, such as increased endothelial permeability and increased leukocyte adhesion. Further, there is the attachment or incorporation of lipoproteins into the vessel wall (see FIG. 1), mainly LDL with its high cholesterol content and very low-density lipoprotein (VLDL), and modification of such lipoproteins by oxidation. Contributory is the adhesion of blood monocytes (and other leukocytes) to the endothelium, followed by migration of monocytes into the intima and their transformation into macrophages and foam cells. The adhesion of platelets to focal areas of denudation or to adherent leukocytes is thought to be involved in the pathology of atherosclerosis as well. In addition, the release of factors from activated platelets, macrophages, or vascular cells that cause migration of smooth muscle cells from media into the intima is likely involved.

Chronic or repetitive endothelial injury may create endothelial stress and to underlie the development of atherosclerosis. Endothelial injury induced in experimental animals by mechanical denudation, hemodynamic forces, immune complex deposition, irradiation, and chemicals causes intimal thickening and, in the presence of high-lipid diets, typical atheromas. Early human lesions, however, develop at sites of morphologically intact endothelium. Thus, non-denuding endothelial dysfunction and activation appear to be more important to the human disease. These are manifested by increased endothelial permeability, enhanced leukocyte adhesion, and alterations in expression of a number of endothelial gene products. For example, endothelial adhesion molecules such as intercellular adhesion molecule-1 (ICAM-1) and vascular cell adhesion molecule-1 (VCAM-1) are expressed in the luminal endothelium overlying developing plaques and are thought to mediate the adhesion of circulating monocytes and lymphocytes during their entry into plaque.

Hyperlipidemia has been shown to be an important contributor to atherosclerosis. Chronic hyperlipidemia, particularly hypercholesterolemia, may impair endothelial function. This may occur through increased production of super-oxide and other oxygen free radicals that deactivate nitric oxide, the major endothelial-relaxing factor. Oxidative stress also activates NF-κB and the endothelial gene expression of numerous biologically active molecules. Furthermore, with chronic hyperlipidemia, lipoproteins accumulate within the intima at sites of increased endothelial permeability. Oxidative modification of lipid by free radicals generated in macrophages or endothelial cells in the arterial wall yields oxidized (modified) LDL. Oxidized LDL, in turn, may contribute to lesion formation because it is readily ingested by macrophages through the scavenger receptor, which is distinct from the LDL receptor, thus forming foam cells. In addition, oxidized LDL is chemotactic for circulating monocytes and it increases monocyte adhesion, largely through the induction of endothelial adhesion molecules. Oxidized LDL also inhibits the motility of macrophages already in lesions, thus favoring the recruitment and retention of macrophages in plaques. The release of growth factors and cytokinesis stimulated by oxidized LDL is cytotoxic to endothelial cells and smooth muscle cells and is immunogenic, inducing the production of antibodies to oxidized lipoproteins. It is this last feature, among other things, that forms the basis of the FIAR test of the present invention.

The pathology of atherosclerosis also involves a role for monocytes that adhere to endothelium early in atherosclerosis via the specific endothelial adhesion of molecules induced on the surface of activated endothelial cells. Monocytes then migrate between endothelial cells to localize subendothelially. There they become transformed into macrophages and avidly engulf lipoproteins, largely oxidized LDL, to become foam cells. In turn, oxidized LDL is chemotactic to monocytes and immobilizes macrophages at sites where it accumulates. Macrophages also proliferate in the intima. If the injury is denuding, platelets also adhere to the endothelium. Macrophages also contribute to the progression of atherosclerotic lesions due to their large number of secretory products and biologic activities. For example, macrophages produce IL-1 and tumor necrosis factor (TNF), which increase adhesion of leukocytes. Several chemokines generated by macrophages (e.g., monocyte chemoattractant protein-1 [MCP-1]) may further recruit leukocytes into the plaque. Macrophages are produced in the lesions, and elaborate growth factors that may contribute to smooth muscle cell proliferation.

The key processes in atherosclerosis are intimal thickening and lipid accumulation, producing the characteristic atheromatous plaques. The atheromatous plaque is the basic lesion consisting of a raised focal plaque within the intima, having a core of lipid (mainly cholesterol and cholesterol esters) and a covering fibrous cap. Also called fibrous, fibro-fatty, lipid, or fibrolipid plaques, atheromatous plaques appear white to whitish yellow and impinge on the lumen of the artery. They vary in size from approximately 0.3 to 1.5 cm in diameter but sometimes coalesce to form larger masses. An alternative term for the atherosclerotic plaque is artheroma. The distribution of atherosclerotic plaques in humans is characteristic. The abdominal aorta is usually much more involved than the thoracic aorta, and aortic lesions tend to be much more prominent around the origins (ostia) of its major branches. Atherosclerotic plaques have three principal components: (1) cells, including smooth muscle cells, macrophages, and other leukocytes; (2) connective tissue extracellular matrix, including collagen, elastic fibers, and proteglycans; and (3) intracellular and extracellular lipid deposits. Fatty streaks are also often observed in the lumen of blood vessels and may be precursors of atheromatous plaques.

Atherosclerotic lesions can be divided into six types, as shown below in Table 1, beginning with isolated foam cells (fatty dots) through stages of fatty streaks, atheromas, and fibroatheromas, to the complicated lesions. The methods of the present invention are useful in monitoring the progression of atherosclerotic disease from its initial stages to its more complex forms. In such a way, treatment methods can be decided upon and instituted as necessary.

TABLE 1

Altherosclerotic Lesions

| Nomenclature | Primary Histology | Sequences in progression |
|---|---|---|
| Type I (initial) lesion | Isolated macrophage foam cells | I |
| Type II (fatty streak) lesion | Mainly intracellular lipid accumulation | II |
| Type III (intermediate) lesion | Type II changes and small extracellular lipid pools | III |

TABLE 1-continued

Altherosclerotic Lesions

| Nomenclature | Primary Histology | Sequences in progression |
|---|---|---|
| Type IV (atheroma) lesion | Type II changes and core of extracellular lipid | IV-VI |
| Type V (fibroatheroma) lesion | Lipid core and fibrotic layer, or multiple lipid cores and fibrotic layers, or mainly calcific, or mainly fibrotic | IV-VI |
| Type VI (complicated) lesion | Surface defect, hematoma-hemorrhage, thrombus | IV-VI |

The methods of the present invention can also be used to monitor the success or failure of treatment for a disease that affects endothelium or that induces the production of reactive oxygen species and lipid oxidation products. Hypertension is a major risk factor for atherosclerosis at all ages, but after age 45 years, hypertension is a stronger risk factor than hypercholesterolemia. Men at age 45 to 62 whose blood pressure exceeds 169/95 mm Hg have a more than fivefold greater risk of ischemic heart disease than those with blood pressures of 140/90 mm Hg or lower. Hypertension accelerates atherosclerosis and causes changes in the structure of the walls of blood vessels that potentiate both aortic dissection and cerebrovascular hemorrhage. In addition, hypertension is associated with the two forms of small blood vessel disease, hyaline arteriolosclerosis and hyperplastic arteriolosclerosis. Both lesions are related to elevations of blood pressure, but other causes may also be involved. Antihypertensive therapy reduces the incidence of atherosclerosis-related diseases, particularly strokes and ischemic heart disease.

Endothelial dysfunction can also involve inflammatory processes. Inflammation of the walls of blood vessels, called vasculitis, is encountered in diverse diseases and clinical settings. Vessels of any type in virtually any organ can be affected. Vasculitis can lead to a wide spectrum of clinical manifestations, which often includes, such as fever, myalgias, athralgias, and malaise. The two most common mechanisms of vasculitis are immune-mediated inflammation and direct invasion of vascular walls by infectious pathogens. Infections can indirectly induce a noninfectious vasculitis, for example, by generating immune complexes or triggering cross-reactivity. Moreover, physical and chemical injury, such as irradiation, mechanical trauma, and toxins, can also cause vascular damage. In such cases, one or a relatively few vessels may be affected, as, for example, in a localized area of infection, irradiation, or mechanical trauma. Occurring chronically, such trauma can contribute to the development of atherosclerosis and other diseases.

The methods of the present invention can also be used to monitor the success or failure of treatment interventions for cigarette smoking that also has a significant deleterious effect on endothelial function. Cigarette smoking is not only a well-established risk factor for atherosclerosis in men, but also is thought to account for the relatively recent increase in the incidence of severity of atherosclerosis in women.

Diabetes mellitus induces hypercholesterolemia and a markedly increased predisposition to atherosclerosis. There is also an increased risk of strokes and, even more striking, perhaps a 100-fold increased risk of atherosclerosis-induced gangrene of the lower extremities. Thus, the methods of the present invention can be used to monitor the progression of treatment for diabetes by monitoring the state of endothelial dysfunction.

Homocystinuria refers to a group of rare inborn errors of metabolism resulting in high levels of circulating homocysteine (>100 μmol/liter) and urinary homocysteine. Patients with this condition have premature vascular disease. Furthermore, elevated levels of homocysteine may be a risk factor for atherosclerosis, coronary artery disease, peripheral vascular disease, stroke, venous thrombosis and neurological disorders such as Parkinson's disease and Alzheimer's. There is evidence that homocysteine may cause endothelial dysfunction, through formation of reactive oxygen species that play an important role in atherosclerosis. It also interferes with the vasodilator and antithrombotic functions of nitric oxide. Hyperhomocystinemia can potentially be caused by low folate and vitamin B intake, and evidence suggests that folate and vitamins $B_6$ and $B_{12}$ ingestion beyond conventional dietary recommendations reduces cardiovascular disease. Thus, the methods of the present invention can be used to monitor the treatment for homocystinemia in order to monitor the state of endothelial dysfunction induced by homocystinemia.

In still other embodiments of the present invention, methods are provided that monitor the progression of a treatment of a vascular disease such as, but not limited to, atherosclerosis. The treatment of a vascular disease can include, but is not limited to, a pharmacological intervention. Such pharmacological interventions can include, but are not limited to, statins. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol. Depending on the agent and the dose used, statins may decrease plasma triglyceride levels and may increase HDL.

Statins are also thought to decrease the generation of oxidized lipid by-products. Because there is increasing evidence that many neurological disorders such as Parkinson's disease or Alzheimer's may be linked to an excess generation of oxidized damaged lipoproteins, patients suffering from these disorders may benefit from statin therapy.

Statins can include, but are not limited to, lovastatin, simvastatin, pravastatin, fluvastatin, cirvastatin, mevastatin, and atorvastatin. Other pharmacological interventions for treatment of a cardiovascular disease include, but are not limited to, bile acid transporter inhibitors such as cholestyramine and colestipol; nicotinic acid (niacin); MTP inhibitors; fibric acid derivatives such as clofibrate, fenofibrate, ciprofibrate, bezafibrate, and gemfibrozil; cholesterol absorption antagonist compounds such as ezetimibe; stanols such as campestanol, cholestanol, clionastanol, coprostanol, 22,23-dihydrobrassicastanol, epicholestanol, fucostanol and stigmastanol; an HDL elevating agent such as a CETP inhibitor; and an ACAT inhibitor such as avasimibe. The methods of the present invention can also be used to monitor the progression of a non-pharmacological treatment on a vascular disease. Such non-pharmacological interventions include, but are not limited to, altered diet and/or exercise.

The present invention also provides methods of monitoring the progression of a cardiovascular disease. The treatment of cardiovascular disease can include, but is not limited to, a pharmacological intervention. Such pharmacological interventions can include, but are not limited to, statins, bile acid transporter inhibitors, MTP inhibitors, cholesterol absorption antagonist compounds, fibric acid derivatives, stanols, an HDL elevating agent, an antihypertensive agent, an ACE inhibitor, a beta andrenergic blocker, an alpha andrenergic blocker, an angiotensin II receptor antagonist, a vasodilator, a diuretic and an anti-inflammatory agent. The methods of the present invention can also be used to monitor the progression of a non-pharmacological treatment on a cardiovascular disease. Such non-pharmacological treatments include, but are not limited to, altered diet, exercise, and dietary or vitamin supplementation.

Fat-Induced Antibody Response (FIAR)

Various embodiments of the present invention comprise the application of the fat-induced acute response or FIAR as described in Le et al., 2000 to methods of: 1) diagnosing and monitoring the progression of an atherosclerotic vascular disease; and, 2) diagnosing and monitoring the progression of a cardiovascular disease. In these embodiments, the amount of endogenous circulating antibodies directed against an oxidatively damaged lipoprotein is measured in a first sample of blood. At least 20 g of polyunsaturated fatty acid is administered to the subject. The polyunsaturated fat can be any single or combination of polyunsaturated fats, including but not limited to, oleic, linoleic, linolenic, or any combination thereof. In some embodiments, the polyunsaturated fatty acid is administered orally in liquid form, capsules or a combination of thereof. In other embodiments, the polyunsaturated fatty acid is administered intravenously as a triglyceride or phospholipid emulsion.

After a period of at least one hour, a second blood sample is taken. In other embodiments, blood samples may be taken on an hourly basis for several hours following the administration of the fat. The amount of endogenous circulating antibodies is then measured in the subsequent samples of blood.

The antibodies measured can be any auto-antibody directed against a modified or oxidized lipoprotein. Non-limiting examples of such antibodies include those disclosed in U.S. Pat. No. 6,309,888 (Holvoet et al.) and U.S. Pat. No. 6,225,070 (Witzum et al.). Thus, in various embodiments, the antibody measured may be directed against low-density lipoprotein, high-density lipoprotein, intermediate density lipoprotein, and very low-density lipoprotein or any combination thereof. In a preferred embodiment, the antibody is directed against an oxidized or modified low-density lipoprotein. In a more preferred embodiment, the antibody is directed against oxidatively damaged malondialdehyde-modified low-density lipoprotein. In still other embodiments, the antibody measured is an IgG-low-density lipoprotein complex.

It is contemplated that the amount of antibody or IgG complex can be measured by any standard method known for such purposes in the art, including but not limited to, ELISA, immunocytochemistry, radiographic or chemoluminescent techniques. As a non-limiting example, the method of Le et al. (2000) can be used. This method utilizes an ELISA with MDA-LDL coated plates to capture the anti-MDA-LDL antibodies present in the blood sample. A second ELISA is used that utilizes a capture antibody isolated by immunoaffinity chromatography directed against human LDL in order to capture the IgG-LDL complex.

Finally, the change in the amount of endogenous circulating antibodies measured is correlated with the severity of the particular disease. Normal to high levels of auto-antibodies are considered to be protective to the individual allowing rapid clearance of oxidized damaged lipoproteins from the circulation before they can cause permanent damage to the endothelium, for example, following a fat-laden meal. In states of endothelial dysfunction, there is generation of oxidized epitopes on damaged lipoproteins in excess of the available auto-antibody reserve following an ingestion of fat. Thus, there is an acute decrease in the amount of circulating auto-antibody. Therefore, the greater the severity of the endothelial dysfunction, the greater the fall in circulating antibodies.

Fat-Induced Acute Response

Other embodiments of the present invention, comprise the application of a variation of the fat-induced antibody response as described above to methods of: 1) monitoring the progression of vascular disease treatment; 2) monitoring the degree of oxidative stress; 3) monitoring the progression of a vascular disease as an indicator of the success or failure of a medical treatment; 4) monitoring the degree of endothelial inflammation; and, 5) diagnosing and monitoring the progression of a cardiovascular disease. In these embodiments, the amounts of lipid oxidation products are measured in a first sample of blood. At least 20 g of polyunsaturated fatty acid is administered to the subject. The polyunsaturated fat can be any single or combination of polyunsaturated fats, including but not limited to, oleic, linoleic, linolenic, or any combination thereof. In some embodiments, the polyunsaturated fatty acid is administered orally in liquid form, capsules or a combination of thereof. In other embodiments, the polyunsaturated fatty acid is administered intravenously as a triglyceride or phospholipid emulsion.

After a period of at least one hour, a second blood sample is taken. In other embodiments, blood samples may be taken on an hourly basis for several hours following the administration of the fat or at any interval determined by the clinician. The amounts of lipid oxidation products are then measured in the subsequent samples of blood. The lipid oxidation products that can be measured include, but are not limited to, malondialdehyde-modified low-density lipoprotein, oxidized low-density lipoprotein, 4-hydroxynonenal-low-density lipoprotein, acetyl-low-density lipoprotein, acrolein-low-density lipoprotein, oxidized arachidonic acid-modified low-density lipoprotein, oxidized linoleic acid modified low-density lipoprotein, lipoperoxide, cardiolipin, oxidized cholesterol, oxidized choleosteryl lineolate, and oxidized triglyceride or any combination thereof.

As one skilled in the art will appreciate, the methods of the present invention are not bound by any methodology, assay or technique that can be used to measure the lipid oxidation products.

Finally, the change in the amount of lipid oxidation products measured is correlated with the severity of the particular disease or with the success or failure of a particular disease treatment. For example, the greater the amount of lipid oxidation products measured would indicate the more severe the vascular disease state or endothelial dysfunction. Conversely, a decrease in the amount of lipid oxidation products would indicate the success of the particular treatment modality being monitored.

All embodiments of the present invention can be performed in any living subject such as mammalian subject without regard for species. In preferred embodiments, the living subject is a human or animal.

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as data are processed, sampled, converted, or the like according to the invention without regard for any particular theory or scheme of action.

EXAMPLES

Example 1

Patient Recruitment/Screening for Fat-Induced Antibody (FIAR) and Fat-Induced Acute Response Test Studies

For all studies, patients were recruited and screened for coronary artery disease (CAD) according to the following criteria.

Study Population: Human subjects with active vascular disease were recruited for this aspect of the study. They were screened by a history and physical exam, measurements of lipid profile and routine blood chemistries to include for example, CBC, TSH, free T4, ALT, AST, CPK, CRP, BUN, creatinine, glucose, hemoglobin A1c (if diabetic), urinalysis for protein and glucose. First preference was given to subjects with coronary artery disease. Exclusions included the use of lipid lowering or high dose angiotensin II—altering (or blocking) drugs within three months of the study. For the purposes of the following example, because of the limitations in finding subjects with coronary artery disease that are not on lipid lowering drugs or other vascular active drugs, subjects were also accepted with high coronary disease risk ratings as determined by Framingham Risk Assessment including both hard and soft risk predictors. These individuals would be expected to have diseased endothelium in spite of the absence of previous history of heart disease. Individuals were also screened using measures of arterial compliance (VASOGRAM) and endothelial reactivity (ENDOGRAM).

Inclusion criteria included the following parameters: 1) ambulatory men of age >40 years old of all ethnicities; 2) ambulatory women of age >50 years old of all ethnicities; 3) LDL concentrations of >130 mg/dl but <250 mg/dl; 4) triglyceride levels of <300 mg/dl; and 5) one or more of the following: (a) Framingham Risk Assessment (Hard Risk) predictive of $\geq 20\%$; (b) Framingham Risk Assessment (Soft Risk) of $\geq 20\%$ in males and $\geq 15\%$ in females; (c) Type II Diabetes mellitus using ADA criteria; (d) convincing evidence of atherosclerotic vascular disease within any vascular field; and (e) abnormal VASOGRAM and/or abnormal ENDOGRAM.

Exclusion criteria included: 1) any acute event caused active arterial disease within the prior three weeks; 2) uncontrolled hypertension (systolic BP>150- or diastolic BP>95); 3) abnormal thyroid function (TSH or free T4 outside the normal range); 4) uncontrolled Type II diabetes or Type I diabetes; 5) active inflammatory disease including liver, renal, or autoimmune disorders; 6) use of any active lipid lowering medication within three months; use of higher doses of any angiotensin II altering or blocking medication within the past 3 months; institution of medications during the previous two months for treatment of diabetes, thyroid disease, high blood pressure, acute infectious process, ovarian failure; 7) consumption of fish oil supplements; and 8) consumption of large doses of substances of significant "antioxidant potential" within two months (vitamins C, E, beta-carotene, etc.).

In initial studies (date not shown) four fat containing meals were administered to groups of volunteers at intervals of approximately one week. The fat content was increased with each fat feeding to provide 8, 16, or 32 grams of polyunsaturated fatty acid (PUFA) either from safflower or from ethyl-EPA. One of the studies contained 16 grams of the alternative oil (safflower or ethyl-EPA). Safflower oil is a mixture of triglycerides containing 74.6% linoleic, 14.2% oleic, 4.3% palmitic, 2% stearic acids and small amounts of other fats. Thus, the 8 grams of linoleate containing meal require 10.7 grams of safflower oil, etc. Ethyl-EPA represents the ethyl ester of eicosapentaenoic acid purified from fish muscle oil and is available in capsules form (99% pure; Laxdale Ltd, Scotland).

Non-invasive tests of arterial compliance (VASOGRAM) and endothelial function were performed before and two and one half (2½) hours after the fatty meal. Endothelial function (ENDOGRAM) was assessed by measuring pulsatile flow in the arm before and after a 5-minute period of ischemia.

All lipid, lipoprotein, and apolipoprotein measurements were performed in the Emory Lipid Research Laboratory, a participant in the NHLBI/CDC Lipid Standardization Program. MDA proteins were measured in the Emory Lipid Research Laboratory using a commercially available kit.

The measurement of the human plasma IgG antibodies to MDA-LDL was accomplished using a "sandwich ELISA" assay consisting of MDA-LDL attached to plastic plates, onto which the plasma was added and incubated allowing the specific antibodies to bind. These were then quantitated by a rabbit anti-human IgG linked to alkaline phosphatase as the signaling molecule.

IgG-LDL immune complexes were measured in the Emory Lipid Research Laboratory using an ELISA consisting of specific antibody to human LDL attached to plastic plates. After incubating human plasma on such plates, the quantity of attached human IgG was measured by the addition of rabbit-alkaline phosphatase complex.

Lipoperoxides were measured using the Free Oxygen Radical Monitor made by INCOMAT MED, GmbH, Germany.

The VASOGRAM, recorded by an FDA approved device supplied by the Vasocor Corporation of Charleston, S.C., was used to measure compliance (VASOGRAM) in the arteries of the thigh and leg and endothelial function in the arm (ENDOGRAM). This evaluation consists of non-invasive measurements that use blood pressure cuffs that are controlled by a computer to make the measurements.

The standardized test meal consisted of a fruit shake prepared with frozen orange juice, nonfat yogurt, sugar and the appropriate amount of oil.

Data Analysis and Sample Size Estimate: Responses were estimated by the area under the curve method with each test meal. Each participant in these studies typically served as his and her own control for the 4 postprandial studies using different types and amounts of fat. This was done to minimize variability in response due to biological factors. Available data would indicate that the gender and ethnic background of the participant had no effect on the FIAR. Assuming a 10% measurement error for the determination of the levels of antibodies in the plasma, it was expected that a 11.14% difference would be detected in AUC between any two test meals by paired 2-tailed t-test with a 90% power from a study population of 12 participants.

Example 2

Fat-Induced Antibody Reduction (FIAR) Test as an Assessment of Endothelial Function Following Statin Therapy

Inventors have previously discovered that patients with atherosclerotic endothelium exhibit an acute and transient reduction in the levels of auto-antibodies against malondialdehyde (MDA)-modified LDL following the consumption of a standardized liquid formula containing polyunsaturated fatty acids (Le et al., 2000). This acute reduction was not observed in young healthy controls with normal endothelium. Though not limited by any particular hypothesis, one explanation for these results is that the interactions of intestinally-derived chylomicrons with the diseased endothelium promote the oxidative modification of dietary polyunsaturated fatty acids resulting in the formation of MDA epitopes in the vascular space.

Figure 3:
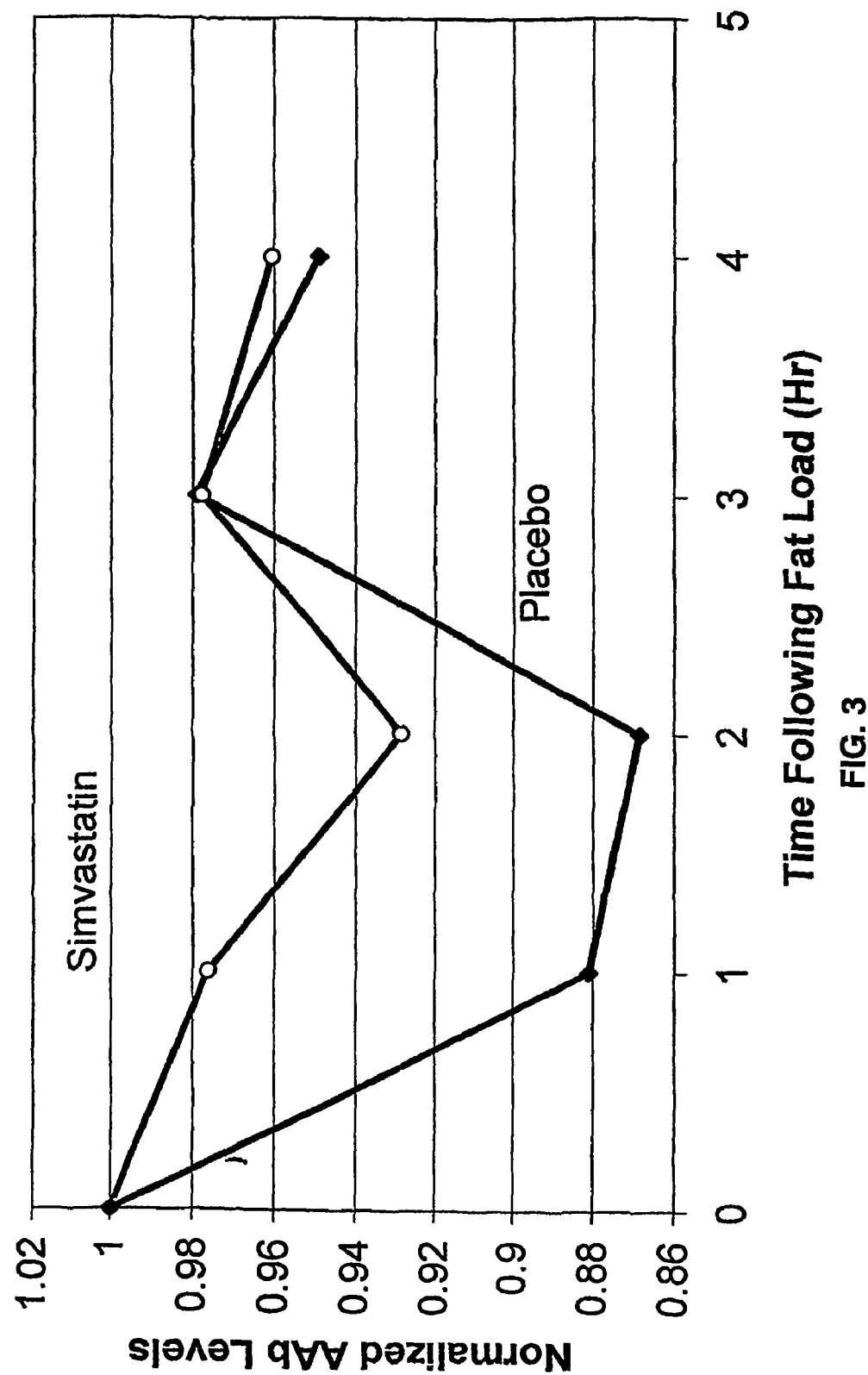
FIG. 3 shows the levels of auto-antibodies against MDA-LDL as determined by ELISA in plasma samples collected at baseline, 1, 2, 3, and 4 hours after the consumption of the fat-containing drink in patients treated with either placebo or simvastatin.
Figure 9:
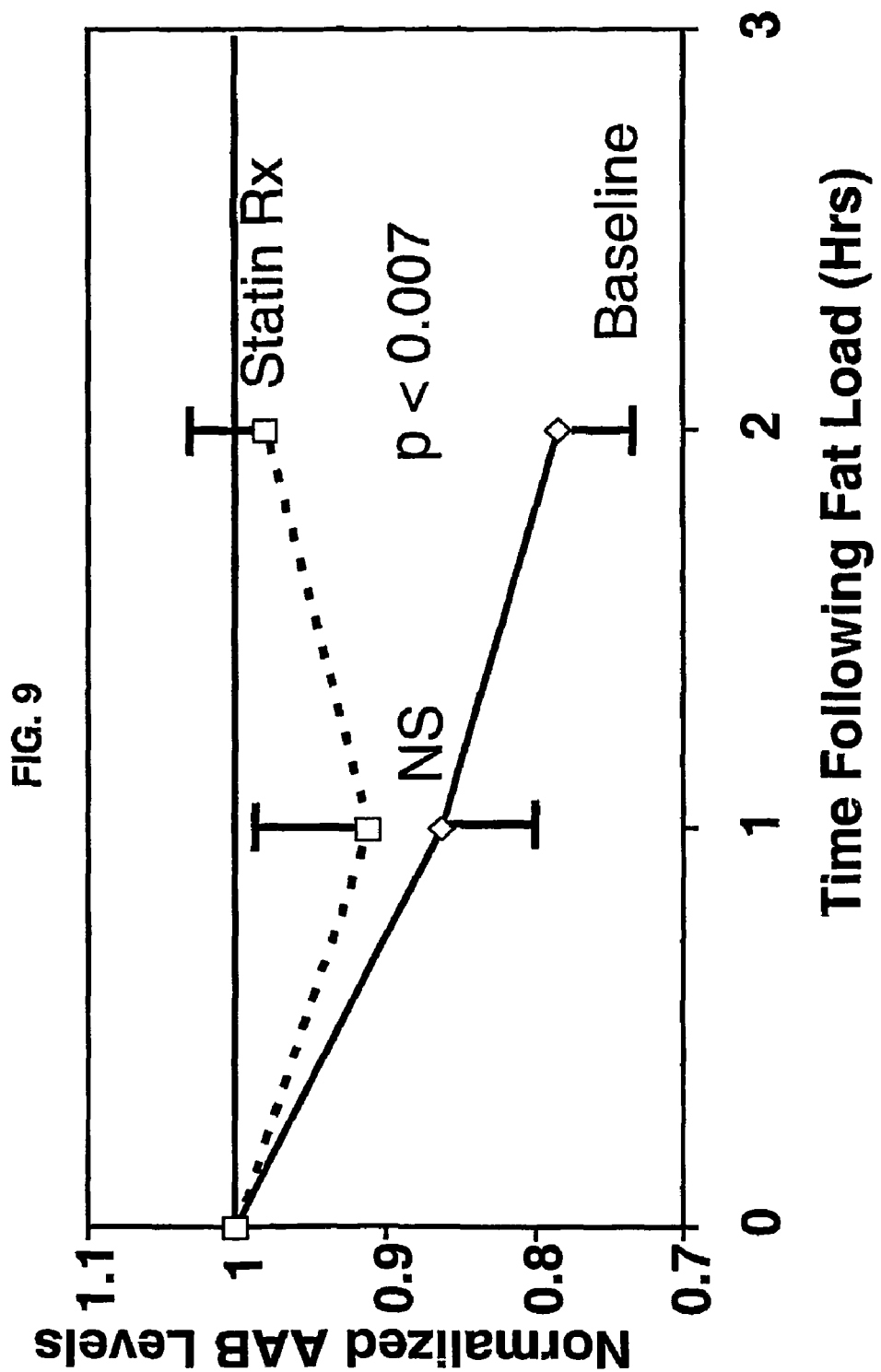
FIG. 9 depicts the partial normalization of the acute antibody response in patients with coronary artery disease following four months of simvastatin treatment.

Statins are an efficient class of agent for the reduction of LDL and have been suggested to reduce oxidation stress on the arterial tree. A study was designed to address whether therapy with simvastatin (40 mg/day) can affect the fat-induced acute response (FIAR) in patients with documented CAD. Thirteen individuals with documented CAD were recruited. Plasma lipids were determined by enzymatic methods. The baseline levels of auto-antibodies against MDA-LDL were determined by ELISA as previously described using plasma samples collected at baseline, 1, 2, 3, and 4 hours after the consumption of the fat-containing drink (FIG. 3). Consistent with earlier studies, FIAR was demonstrated in all subjects with documented CAD with the maximum reduction of 15% in AAb levels occurring at 2-hr after the test meal. The area under the 4-hr displacement curve was statistically significant ($p<0.002$) using two-tailed paired t-test. After 4 months on therapy, LDL levels were reduced by an average of 32.1% (data not shown). FIAR was significantly reduced after simvastatin therapy for the two-hour time point (FIG. 9) indicating a partial recovery in endothelial function. The present data would suggest that statin therapy has a direct effect on endothelial dysfunction by reducing the propensity of the arterial wall to generate oxidatively modified epitopes and that FIAR is a useful biochemical assessment of endothelial dysfunction.

Example 3

Acute In Vivo Generation of Oxidatively Modified Epitopes During Postprandial Lipemia in Patients with Coronary Artery Disease (CAD)

Case-control studies in humans have resulted in contradictory findings suggesting that controls groups have higher auto-antibody titers as compared to patients with documented CAD. Other studies have shown the opposite results. One purpose of this study was to utilize FIAR to assess endothelial function in patients with CAD. Patients with CAD were selected as described in Example 1. The FIAR test was administered as detailed in the previous examples.

Patients with documented CAD were admitted to the General Clinical Research Center (GCRC) on the afternoon before the study was scheduled. They received a standardized low-fat dinner at 6 p.m. and remained fasted until 8 a.m. the next morning. Control participants were asked to consume their usual dinner before 6 p.m. and report to the GCRC by 7 a.m. on the day of the study. The standardized test meal consisted of a fruit shake prepared with frozen orange juice, nonfat yogurt, sugar, Lipomul (Upjohn, Kalamazoo, Mich.), and the yolks from 2 medium hard-boiled eggs. Blood samples were collected in EDTA every hour after ingestion of the meal. The plasma was isolated within one hour and several aliquots were made. All plasma samples were stored at $-70°$ C. in 0.5 ml aliquots until analysis (3 to 6 months). Only the fasting, 2-hour, 4-hour, and 6-hour samples that were never thawed and refrozen were analyzed.

Figure 4:
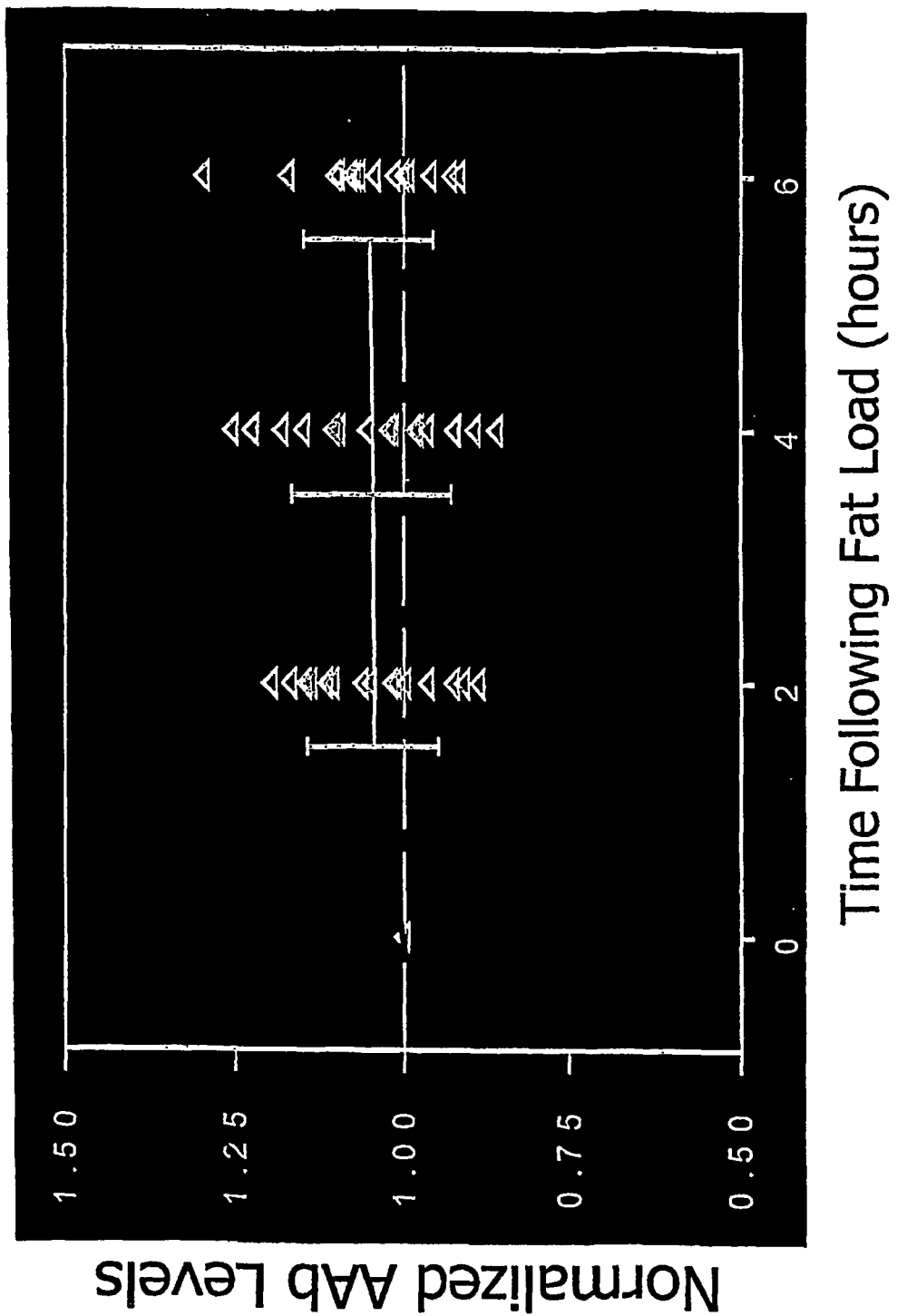
FIG. 4 shows the results from a previous study (Le et al., 2000) in which no alterations in auto-antibody titers were observed in subjects with healthy endothelium.
Figure 5:
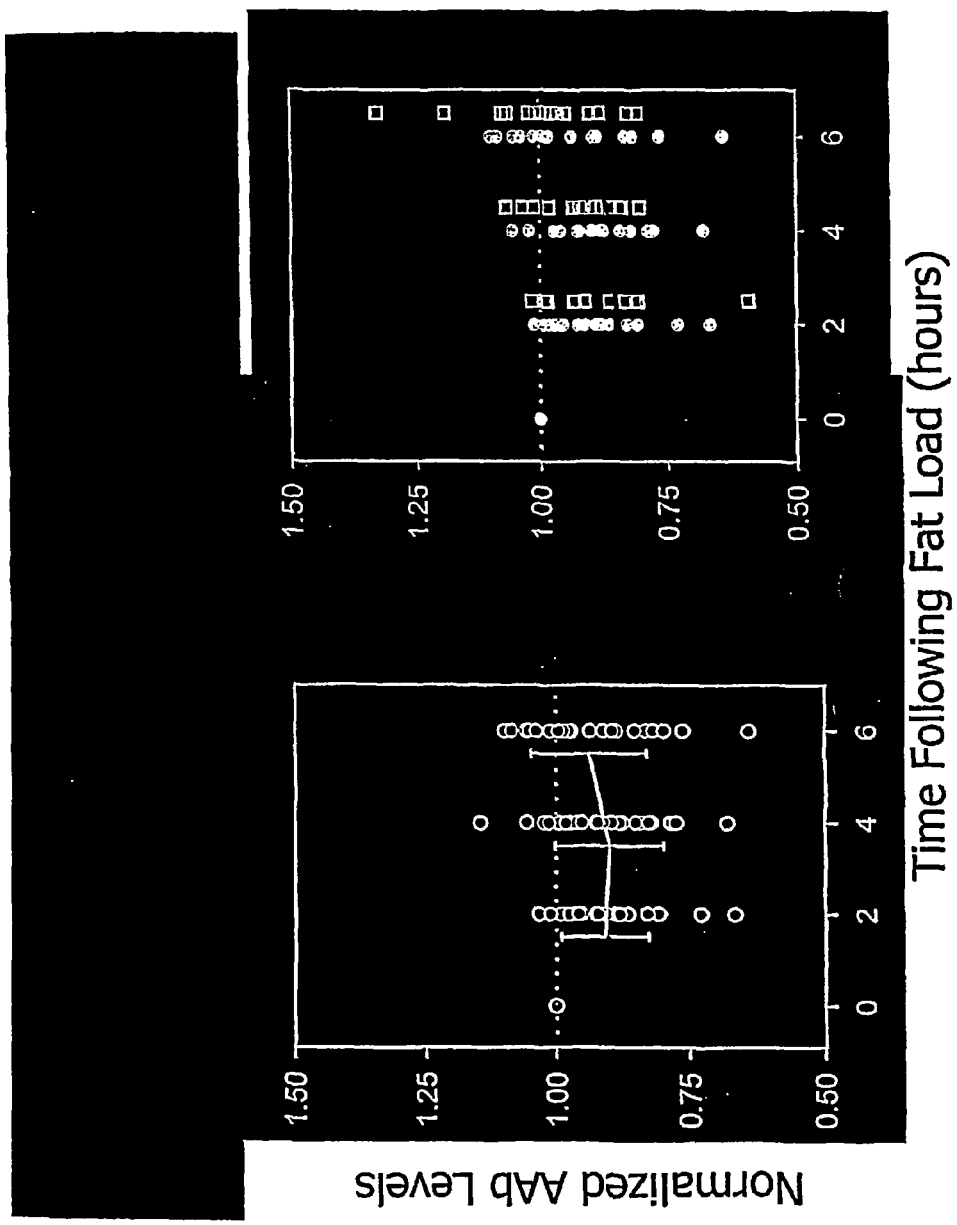
FIG. 5 depicts the transient fat-induced decrease in auto-antibody titers observed in patients with coronary artery disease.

FIG. 4 shows the results from a previous study in which no alterations in auto-antibodies titers were observed in subjects with healthy endothelium (Le et al., 2000). In contrast, FIG. 5 shows that auto-antibody titers were transiently reduced (panel B) in patents with documented CAD.

Example 4

Determination of the Optimal Type of Polyunsaturated Free Fatty Acid for Use in the Fat-Induced Antibody Response (FIAR) Test in Patients with CAD Ten patients with demonstrated CAD were selected as in the previous example. The FIAR test was administered as described in the previous examples. Four different test meals were examined each containing as the primary source of fat: 1) safflower oil (polyunsaturated); 2) coconut oil (monounsaturated); 3) canola oil (saturated); and 4) carbohydrates only (no fat). Each participant received all four test meals in random order on four separate occasions. Each study was separated by approximately five to seven days. Hourly blood samples were collected for a total of six hours. Auto-antibody levels were determined as described in Example 5 by ELISA using freshly prepared MDA-LDL as the capture antigen and alkaline phosphates-conjugated goat anti-human IgG for detection.

Figure 6:
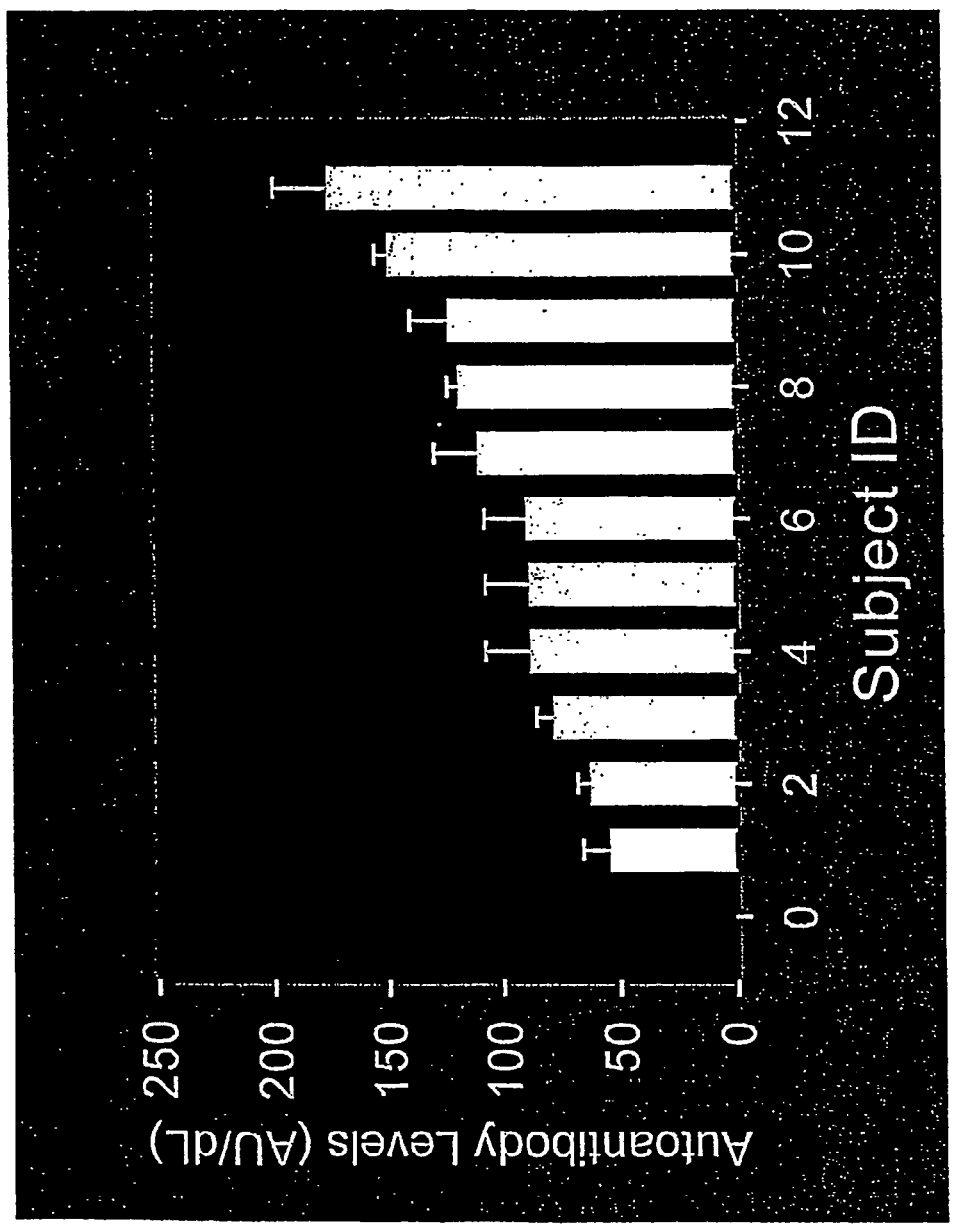
FIG. 6 shows the baseline auto-antibody titers in 10 subjects with coronary artery disease.
Figures 8A, 8B, 8C, 8D:
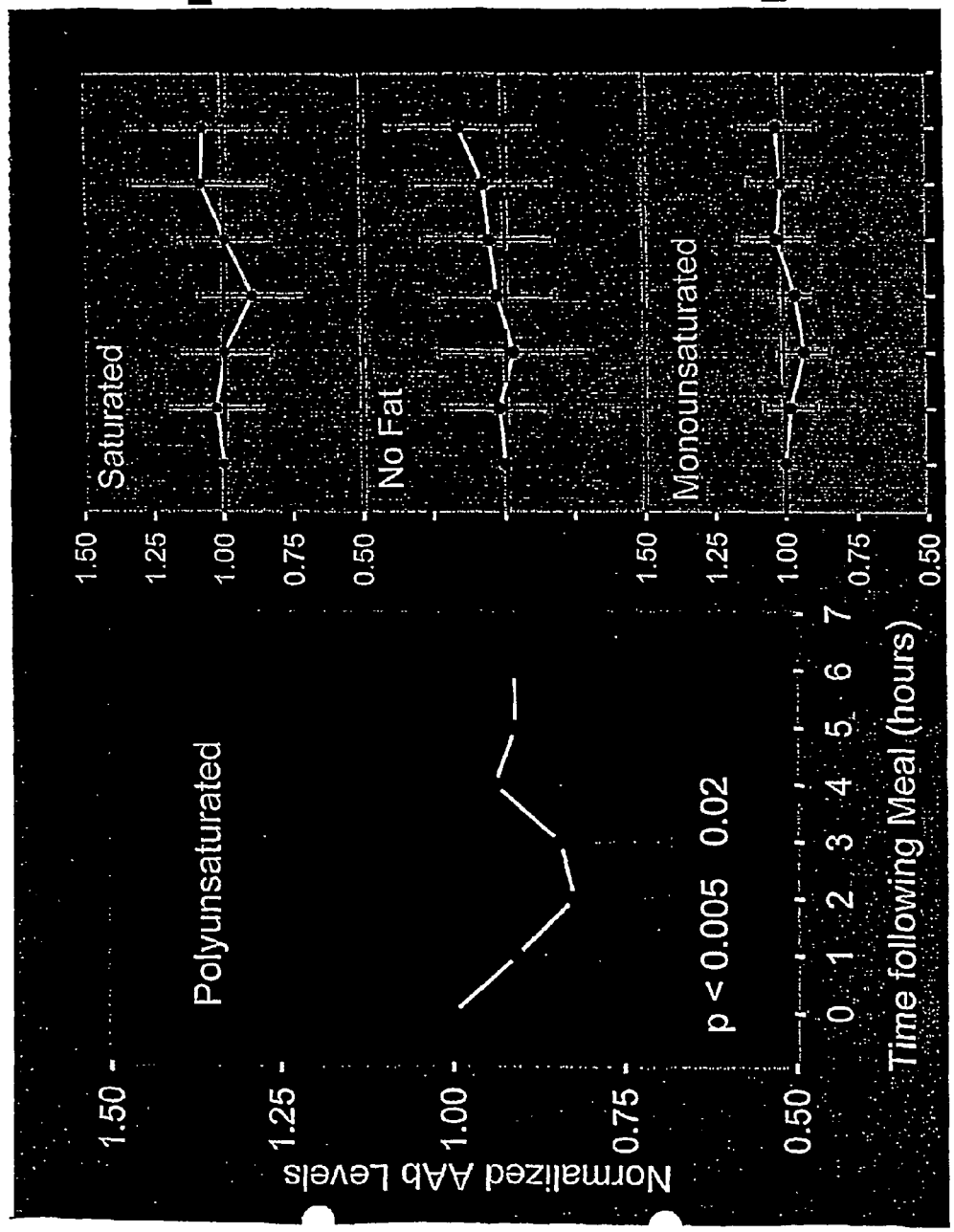
FIGS. 8A-D show normalized trigyliceride levels following a saturated fat (A), carbohydrate only (no fat; B), polyunsaturated fat (C) and monounsaturated fat (D) meal.

FIG. 6 shows the baseline auto-antibody titers in the 10 subjects. Baseline titers range from approximately 10 AU/dl to 150 AU/dl. FIG. 7 shows normalized triglyceride levels following the saturated fat (A), carbohydrate only (no fat; B), polyunsaturated fat (C) and monounsaturated fat (D) meals. Triglyceride levels were significantly increased up to six hours after the all meals except the carbohydrate only meal. FIG. 8 shows normalized auto-antibody (AAb) levels following all four meals. Panel A depicts the transient decrease in AAb levels following the polyunsaturated fat meal. The acute transient response was also shown to be dose-dependant (data not shown) with a mean reduction of 10% following a meal with 25 grams of polyunsaturated fat and a mean reduction of 23% following a meal with 50 grams of polyunsaturated fat.

Thus, in spite of comparable increases in postprandial triglycerides, test meals containing monounsaturated (coconut oil) or unsaturated (canola oil) fat did not produce any transient reduction in auto-antibody levels. The test meal containing only carbohydrate produces no increases in postprandial triglycerides and did not induce the transient response in auto-antibody levels.

The attachment of triglyceride-rich lipoproteins to the endothelium, most likely creates a microenvironment that facilitates the transfer of oxidative radicals from the damaged endothelium on the plasma lipoproteins. Thus, during postprandial lipemia, the flux of dietary polyunsaturated fatty acids results in a transient reduction in the circulating levels of auto-antibodies against MDA-modified LDL. The applicants have demonstrated this only occurs in patients with diseased endothelium such as CAD patients and does not occur in normal, healthy endothelium.

Example 5

ELISA for MDA-LDL Antibodies

The following procedures were used in the preceding examples to measure the levels of circulating auto-antibodies.

Preparation of MDA-LDL: A stock MDA solution was prepared by mixing 0.6 mL MDA-acetal with 1.9 mL 0.2-mol/L HCl. The mixture was allowed to incubate for ten minutes at $37°$ C. The reaction was stopped by the addition of 1.4 mL, 1.0 mol/L KOH, and the mixture was adjusted to pH 7.4 before adjustment to a final volume of 5 mL with distilled H$_2$O. This stock solution was prepared fresh and used on the same day. Pooled plasma was used to isolate LDL at density 1.020 to 1.063 g/mL by sequential ultracentrifugation using a fixed-angle rotor (Beckman 50.4 Ti; Beckman Instruments, Fullerton, Calif.). The isolated LDL was dialyzed against 0.15 mol/L NaCl containing EDTA (pH 7.4). Freshly prepared MDA solution was added to LDL at 120 μL/mg LDL protein, and the mixture was allowed to incubate at 37° C. for 2.5 hours. The mixture was subsequently extensively dialyzed against phosphate-buffered saline (PBS) containing one mmol/L EDTA and subjected to centrifugation at 12,000 rpm for 10 minutes to remove any aggregate. The modified LDL was used to coat 96-well ELISA plates that can be stored at −20° C. for up to 8 weeks.

Calibration of the ELISA System: A plasma pool that was prepared from fresh plasma obtained in a group of 100 free-living individuals participating in a worksite cholesterol-screening program was assigned an arbitrary level of 100 AU/dL and designated as the primary calibrator. Three separate plasma pools were prepared according to the optical densities obtained from the application of a 1:500 dilution in wells previously coated with MDA-LDL.

ELISA for Antibodies Against MDA-LDL: The plates were coated with 100 μL MDA-LDL (100 μg/mL) diluted in 50 mmol/L PBS (containing 0.1 mmol/L NaCl, and 0.001 mol/L EDTA, pH 7.4) for 16 hours at 4° C. After extensive washing (borate buffer with 0.1% Tween-20), the plates were blocked with a solution of human serum albumin (3 mg/mL) diluted in PBS (16 hours at 4° C.). Dilutions of plasma (typically 1:500) were applied to the plate (100 μL) in triplicate and allowed to incubate for 16 hours at 4° C. Detection was achieved with a 1:2,000 dilution of a commercially available goat anti-human immunoglobulin G conjugated with alkaline phosphatase (BioRad Laboratories, Richmond, Calif.).

Using the primary pool with an assigned concentration of 100 AU/dL as a calibrator, the AAb levels (mean±SD) in the standard, high control (QC1), and low control (QC2) are 167±10.5, 73.4±9.8, and 43.7±3.9 AU/dL, respectively. In all subsequent analyses, dilutions of the standard pool were used to construct a standard curve and the QC1 and QC2 pools were included as quality controls. The standard, QC1, and QC2 pools were stored at −80° C. in small aliquots and thawed once for each assay and discarded. When a new pool had to be used for standard, AAb levels in this pooled sample were defined against the standard currently in use and the primary calibrator to ensure comparability of the assays.

ELISA for Soluble Immune Complexes: This assay is specific for LDL-IgG immune complexes (ICs). The capture antibody was a specific goat IgG isolated by immunoaffinity chromatography against human LDL, and the detection antibody was a commercially available alkaline phosphatase—coupled goat IgG against human IgG. For this assay, a solution of milk protein (2 mg/mL) was used as the blocking agent. Standardization of this assay was similar to the process described for the AAb assay using the same plasma pools as standard and quality controls. The mean concentration in the standard, QC1, and QC2 pools were 91.3±12.8, 106.4±15.0, and 49.5±6.4 AU/dL.

The above specification, examples and data provide a complete description of the manufacture and use of the composition of the invention. Since many embodiments of the invention can be made without departing from the spirit and scope of the invention, the invention resides in the claims hereinafter appended.

---

List of References

1. Alberti A, Bolognini L, Macciantelli D, and Caratelli M. The Radical Cation of N,N-Diethyl-para-Phenylendiamine: A Possible Indicator of Oxidative Stress in Biological Samples. Res. Chem. Intermed. 2000 Vol 26(3):253-267.
2. Avogaro P, Bittolo B, Cazzolato G. Presence of modified LDL in humans. Arteriosclerosis. 1988; 8:79-87.
3. Esterbauer H, Gebicki J, Puhl H, and Jurgens G. The role of lipid peroxidation and antioxidants in oxidative modification of LDL. Free Radical Biol Med. 1992; 13:341-390.
4. Ginsberg H N, N-A Le, and J C Gibson (1985) Regulation of the production and catabolism of plasma LDL in hypertriglyceridemic subjects: Effect of weight loss. JCI 75: 614-622.
5. Holvoet P, Perez G, Zhao Z, et al. Malondialdehyde-modified LDL in patients with atherosclerotic disease. J Clin Invest. 1995; 95:261 1-2619.
6. Le N A, Li X, Kyung S, Brown W V. Evidence for the in vivo generation of oxidatively modified epitopes in patients with atherosclerotic endothelium. Metabolism: Clinical & Experimental. 2000; 49(10):1271-7.
7. Ludmer P L, Selwyn A P, Shook T L, Wayne R R, Mudge G H, Alexander R W, Ganz P. Paradoxical vasoconstriction induced by acetlycholine in atherosclerotic coronary arteries. NEJM. 1986; 315:1046-105.
8. Nabel E G, Selwyn A P, Ganz P. Large coronary arteries in humans are responsive to changing blood flow: an endothelium-dependent mechanism that fails in patients with atherosclerosis. J AM Call Cardiol. 1994; 16:349-356.
9. Pentikainen M O, R Oksjoki, K Oorni and P T Kovanen (2002) Lipoprotein lipase in the arterial wall: Linking LDL to the arterial extracellular matrix and much more. ATVB 22:211-217.
10. Ross R (1999) Atherosclerosis—an inflammatory disease. NBJM 340: 115-149.
11. Treasure C B, Klein J L, Weintraub W S, Talley J D, Stillabower M E, Kosinski A S, Zhang J, Boccuzzi S J, Cedarholm J C, Alexander R W. Beneficial effects of cholesterol-lowering therapy on the coronary endothelium in patients with coronary artery disease. NEJM. 1995; 332(8):481-7.
12. Vogel R A (1997) Coronary risk factors, endothelial function and atherosclerosis: a review. Clin Cardiol 20: 426-432.
13. Wilkinson I, Qasem A, McEniery C, Webb D, Avolio A, Cockcroft J. Nitric Oxide Regulates Local Arterial Distensibility in Vivo. Circulation 2002; 105:213-217.
14. Wilson, Peter W F, D'Agostino, R, Levy, D, Belanger, A., Silbershatz, H, Kannel, W. Prediction of Coronary Heart Disease Using Risk Factor Categories. Circulation 1998; 97(18):1837-1847.
15. Yla-Herttuala S, Palinski W, Butler S, et al. Rabbit and human atherosclerotic lesions contain IgG that recognizes epitopes of oxidized LDL. Arterioscler Thromb. 1994; 14:32-40.
16. Yla-Herttuala S, Palinski W, Rosenfeld M, et al. Evidence for the presence of oxidatively modified LDL in atherosclerotic lesions of rabbit and man. J Clin Invest. 1989; 84:1086-1095.
17. Zilversmit D B (1973) A proposal linking atherogenesis to the interaction of endothelial lipase with TG-rich lipoproteins. Circ res 33: 633-638.
18. Zilversmit D B (1979) Atherogenesis: a postprandial phenomenon. Circulation 60: 473-485.

We claim:

1. A method of diagnosing a vascular disease, wherein said vascular disease is at least one selected from the group consisting of atherosclerosis and thrombosis, in a living subject, comprising the steps of: (a) measuring the amount of endogenous circulating antibodies directed against an oxidatively damaged low-density lipoprotein in a sample of blood from the living subject; (b) administering a polyunsaturated fatty acid to the living subject; (c) measuring the amount of said endogenous circulating antibodies in a second sample of blood from the living subject obtained after the administration of said polyunsaturated fatty acid; and, (d) determining the difference in the amount of said endogenous circulating antibodies between (a) and (c), wherein said antibodies do not interact with intestinally-derived chylomicrons and wherein the greater the severity of the vascular disease, the greater the fall in said circulating antibodies.

2. The method of claim 1, wherein the vascular disease is atherosclerosis.

3. The method of claim 1, wherein the low-density lipoprotein is malondialdehyde-modified low-density lipoprotein.

4. The method of claim 1, wherein the antibody is an IgG antibody.

5. The method of claim 1, wherein the polyunsaturated fatty acid is administered orally.

6. The method of claim 1, wherein the polyunsaturated fatty acid is a triglyceride.

7. The method of claim 1, wherein the polyunsaturated fatty acid is a phospholipid emulsion.

8. The method of claim 1, wherein the living subject is a human.

9. The method of claim 1, further comprising: (e) making a diagnosis based on the result of (d).

10. The method of claim 1, wherein the circulating antibodies directed against an oxidatively damaged low-density lipoprotein include antibodies directed against malondialdehyde-modified low-density lipoprotein, 4-hydroxynonenal-low-density lipoprotein, acetyl-low-density lipoprotein, acrolein-low-density lipoprotein, oxidized arachidonic acid-modified low-density lipoprotein, oxidized linoleic acid modified low-density lipoprotein, lipoperoxide, cardiolipin, oxidized cholesterol, oxidized choleosteryl lineolate, and oxidized triglyceride.

* * * * *